United States Patent
Bravo

(10) Patent No.: US 9,976,842 B2
(45) Date of Patent: May 22, 2018

(54) DEVICE AND METHOD FOR DETECTING DEFECTS DURING SEALING OF A PACKAGE COMPRISING A FOIL

(71) Applicant: QIPACK BVBA, Haasrode (BE)

(72) Inventor: Cédric Daniel Kathleen Philippe Bravo, Haasrode (BE)

(73) Assignee: QIPACK BVBA, Haasrode (BE)

( * ) Notice: Subject to any disclaimer, the term of this patent is extended or adjusted under 35 U.S.C. 154(b) by 280 days.

(21) Appl. No.: 14/372,881

(22) PCT Filed: Jan. 17, 2013

(86) PCT No.: PCT/IB2013/050424
§ 371 (c)(1),
(2) Date: Jul. 17, 2014

(87) PCT Pub. No.: WO2013/108202
PCT Pub. Date: Jul. 25, 2013

(65) Prior Publication Data
US 2015/0028860 A1    Jan. 29, 2015

(30) Foreign Application Priority Data

Jan. 17, 2012  (NL) ..................................... 2008129

(51) Int. Cl.
*G01N 21/00*   (2006.01)
*B29C 65/00*   (2006.01)
(Continued)

(52) U.S. Cl.
CPC ................ *G01B 7/14* (2013.01); *B29C 65/18* (2013.01); *B29C 65/8253* (2013.01);
(Continued)

(58) Field of Classification Search
None
See application file for complete search history.

(56) References Cited

U.S. PATENT DOCUMENTS

| 5,147,491 A | 9/1992 | Thomas et al. |
| 5,551,206 A | 9/1996 | Fukuda |

(Continued)

FOREIGN PATENT DOCUMENTS

| EP | 0865989 A2 | 9/1998 |
| EP | 1127794 A2 | 8/2001 |

(Continued)

OTHER PUBLICATIONS

Yamamoto et al JP 2007191197, "Packaging Apparatus", (English Machine Translation) Published Aug. 2, 2007.*

(Continued)

*Primary Examiner* — Farhana Hoque
(74) *Attorney, Agent, or Firm* — Maier & Maier, PLLC

(57) ABSTRACT

A device for detecting defects during sealing of a package including a foil, and a method for detecting defects during sealing of a package including a foil which makes use of such a device. The device may include a distance sensor for determining the distance between at least two clamping elements, and a control unit coupled to the distance sensor for comparing the measured distances to predefined references. Such a device may be operated by, for example, positioning a foil and another part of a package to be connected to the foil between the clamping elements, moving the clamping elements toward one another until a connection between the foil and the other part of the package is formed, determining the distance between the clamping elements over a period, moving the clamping elements apart, and removing the package.

17 Claims, 2 Drawing Sheets

Figure 1:
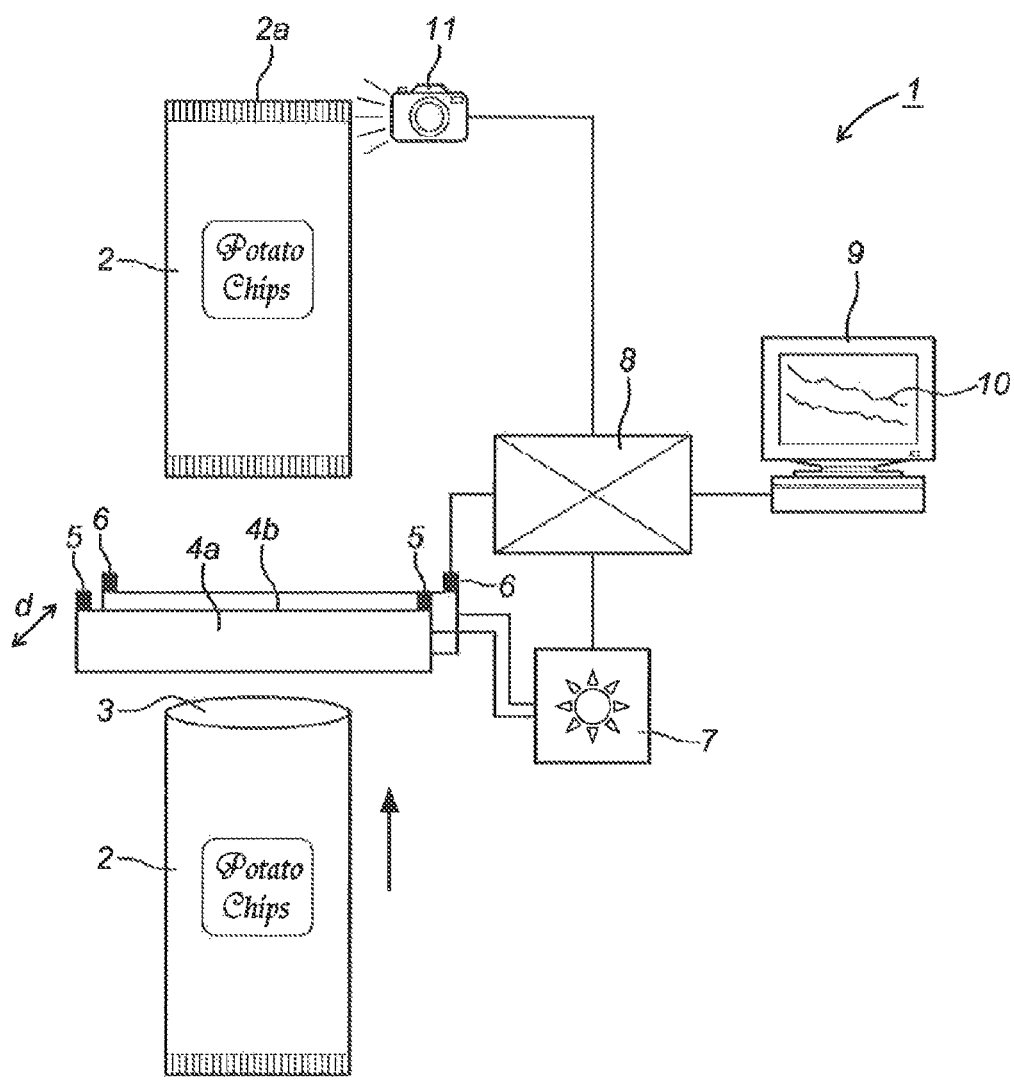

(51) Int. Cl.

| | |
|---|---|
| *G01B 7/14* | (2006.01) |
| *B29C 65/18* | (2006.01) |
| *B29C 65/82* | (2006.01) |
| *B65B 51/14* | (2006.01) |
| *B65B 7/06* | (2006.01) |
| *G01B 11/14* | (2006.01) |
| *B29C 65/08* | (2006.01) |
| *B29C 65/48* | (2006.01) |
| *B65B 51/30* | (2006.01) |
| *G01N 21/88* | (2006.01) |
| *B29C 65/04* | (2006.01) |

(52) U.S. Cl.
CPC ........ *B29C 66/1122* (2013.01); *B29C 66/342* (2013.01); *B29C 66/43121* (2013.01); *B29C 66/8161* (2013.01); *B29C 66/81435* (2013.01); *B29C 66/8227* (2013.01); *B29C 66/8322* (2013.01); *B29C 66/849* (2013.01); *B29C 66/929* (2013.01); *B29C 66/9292* (2013.01); *B29C 66/92311* (2013.01); *B29C 66/92611* (2013.01); *B29C 66/961* (2013.01); *B65B 7/06* (2013.01); *B65B 51/146* (2013.01); *G01B 11/14* (2013.01); *B29C 65/04* (2013.01); *B29C 65/08* (2013.01); *B29C 65/48* (2013.01); *B29C 66/7352* (2013.01); *B29C 66/7373* (2013.01); *B29C 66/81417* (2013.01); *B29C 66/8242* (2013.01); *B29C 66/8491* (2013.01); *B29C 66/919* (2013.01); *B29C 66/9192* (2013.01); *B65B 51/303* (2013.01); *G01N 21/8806* (2013.01)

(56) References Cited

U.S. PATENT DOCUMENTS

| | | | |
|---|---|---|---|
| 6,167,677 B1 | 1/2001 | Kammler et al. | |
| 6,288,554 B1* | 9/2001 | Yasumoto | G01N 27/61 324/558 |
| 7,061,249 B2* | 6/2006 | Otsuka | B29C 66/1122 324/519 |
| 2008/0115566 A1* | 5/2008 | Van Rootselaar | G01M 3/36 73/49.3 |
| 2008/0212086 A1* | 9/2008 | Antonacci | G01N 21/3563 356/239.4 |
| 2011/0094195 A1 | 4/2011 | Bartoli et al. | |

FOREIGN PATENT DOCUMENTS

| | | | |
|---|---|---|---|
| EP | 1645401 A2 | | 4/2006 |
| JP | 02-045308 A | | 2/1990 |
| JP | 7-187153 A | | 7/1995 |
| JP | 9-221111 A | | 8/1997 |
| JP | 2003-112714 A | | 4/2003 |
| JP | 2004-268932 A | | 9/2004 |
| JP | 2006-321549 A | | 11/2006 |
| JP | 2007-191197 A | | 8/2007 |
| JP | 2007191197 A | * | 8/2007 |

OTHER PUBLICATIONS

Ozguler et al, "Ultrasonic Imaging of Micro-Leaks and Seal Contamination in Flexible Food Packages by the Pulse-Echo Technique", Journal of Food Science, vol. 63, No. 4 (Published 1998), pp. 673-678.*
Iwase Tatsuhiko, JP 2004268932, "Sealing Device and Seal Control Method", English Machine Translation, Published Sep. 30, 2004.*
Yamamoto et al, "Packaging Apparatus", JP 2007191197, English Machine Translation, Published Aug. 2, 2007.*
International Search Report and Written Opinion dated Jun. 12, 2013 from corresponding International Patent Application No. PCT/IB2013/050424; 11 pgs.
International Search Report dated Jun. 27, 2012 from corresponding Netherlands Patent Application No. NL2008129.
Database WPI week 200753; Thomson Scientific, London, GB; AN 2007-540406; X002678755; JP 2007 191197 A (Ishida Koki Seisakusho KK); Aug. 2, 2007; 1 pg.
Japanese Office Action dated Jan. 5, 2017, in connection with corresponding JP Application No. 2014-552732 (9 pgs., including English translation).
European Third Party Observations dated Dec. 1, 2016, in connection with EP Application No. 13710548.2, including cited non-patent literature articles by Ostyn, et al. and Ozguler, et al. (62 pgs.).
Bert Ostyn, et al., "Statistical Monitoring of a Sealing Process by Means of Multivariate Accelerometer Data", in Quality Engineering, vol. 19, 2007, pp. 299-310 (13 pgs.).
European Communication pursuant to Rule 114(2) EPC (Third-party observation (TPO)) dated Dec. 11, 2017, in connection with EP Application No. 13710548.2 (68 pgs.).

* cited by examiner

DEVICE AND METHOD FOR DETECTING DEFECTS DURING SEALING OF A PACKAGE COMPRISING A FOIL

The invention relates to a device for detecting defects during sealing of a package comprising a foil. The invention also relates to a method for detecting defects during sealing of a package comprising a foil, particularly by making use of the device according to the invention.

A wide range of products is packaged in an airtight (sealed) package so as to increase the shelf life of the products, guarantee quality and/or maintain sterility. Such products vary from food and beverages and medical, electrical and pharmaceutical products to liquids, solids, gases or a combination thereof. A crucial part of the packaging process is to ensure a high-quality sealing of the package. The quality is particularly determined here by the airtightness, but may also relate to other aspects such as inclusions, strength and visual appearance. In the case the seal (package weld seam) does not comply with the set quality requirements, particularly in that the seal is not airtight, the quality of the packaged product may degrade relatively quickly, which can compromise the microbiological safety and thereby endanger the health of the consumer. Insufficient seal quality is a common problem in the packaging industry. Since this problem has consequences for the safety of consumers, and generally also for the market behaviour of consumers, the packaging industry is particularly sensitive to this problem. Manual monitoring of individual packages is usually a time-consuming and costly activity.

An object of the present invention is to provide a device with which defects can be detected during sealing of packages.

The invention provides for this purpose a device of the type stated in the preamble, comprising: at least one distance sensor for determining the distance between at least two relatively displaceable clamping elements for pressing against each other the foil and another part of the package to be attached to the foil, and at least one control unit coupled to the at least one distance sensor for comparing the measured values collected by the distance sensor to predefined reference measured values for a period during displacement of the clamping elements toward each other. By measuring the actual distances between the clamping elements and comparing them to representative reference values as a function of the time progression of the sealing process, on the basis of which the relative displacement speed of the clamping elements can be determined by means of the control unit, defects can be detected relatively quickly, accurately and reliably during the sealing. In the case air, a liquid and/or a solid particle is enclosed between the foil and the other part of the package, the distance detected between the clamping elements will be greater than, or at least differ from, the predefined reference values, whereby inclusions can be detected and (the seriousness of) the defect in the seal can be determined The seriousness of the defect is usually related here to the extent to which the detected distances differ from the reference values. Measuring the relative displacement speed of the clamping elements, or at least determining this by means of calculation, moreover makes it possible to monitor and determine the mutual fusing of the foil and the other part of the package, generally also formed by another part of the same foil. During fusing together of the two package parts there will be an instantaneous, relatively strong increase in the relative displacement speed of the clamping elements, which can be detected relatively easily by means of the device according to the invention and which is indicative of the quality of the seal created in the package. Such a detection is thus only possible when the distance between the clamping elements is measured as a function of time, continuously or discontinuously, during the closing of the clamping elements, on the basis of which the relative displacement speed of the clamping elements during the closing process can be determined Only measuring the distance between the clamping elements and optionally comparing these distances to reference values has been found insufficient for this purpose. Determining the distance between the clamping elements takes place by applying one or more distance sensors. These distance sensors are adapted to measure the distance of at least one clamping element relative to a reference location, wherein the reference location can be formed by an (opposite) clamping element, whereby the distance between the clamping elements can be measured directly. In the case the reference location is formed by a stationary element, the distance between the clamping elements will then be measured indirectly (via the reference location). The device according to the invention thus forms in the first instance a detection device for quality control of a seal of a package comprising a foil. The device can have been or can be integrated into an existing packaging line, although it is also possible to envisage the device co-acting as (releasable) module with an existing packaging line. The control unit can also be referred to as data-processing unit, since the control unit is particularly adapted to process detected measured values.

In a preferred embodiment of the device according to the invention the device comprises a signal generator coupled to the control unit for generating a signal when the control unit determines that at least one detected measured value exceeds at least one reference value. The generated signal can here be of electrical, auditive and/or visual nature. The signal generally has the purpose of generating a warning to a person operating the device that a manufactured seal has one or more defects, after which the person can optionally remove the defective package from the production line. The control unit can here activate the signal generator at the moment that a detected measured value just exceeds a reference value, although it is also possible to envisage the control unit only activating the signal generator after the measured value exceeds the reference value by a predetermined absolute or relative (error) margin.

The distance between the clamping elements is monitored during at least a period of the closing process, wherein the measured values are compared to predefined reference values related to the progress of the closing process. The whole closing process can be monitored here, although it is generally more advisable to monitor only a specific critical period of the closing process. It is particularly advantageous here that the closing process, wherein the clamping elements are moved from a (fully) opened position all the way toward each other, has a duration of x seconds, wherein the distance between the clamping elements is measured for between 0.2x and 5x seconds, particularly between 0.4x and 2x seconds, more particularly between 0.4x and x. This means that the measured values are collected and compared to the reference values during the final 80% or 60% of the time taken by the closing process. It is also possible to envisage the above stated critical period not being determined subject to time but subject to the course of the process. It is advantageous here for the closing process, wherein the clamping elements are moved all the way toward each other from an opened position, to have a progression y, wherein the distance between the clamping elements is measured at least between 0.2y and y, particularly between 0.6y and y. This means that the measured values are collected and are compared to the reference values during the final 80% or 40% of the actual process. The measured values can be collected continuously or discontinuously. When the measured values are collected discontinuously, a measured value is collected a short period (several milliseconds or shorter) after a previous measured value has been collected. The total measured values result in a measuring curve which can be displayed graphically on a screen coupled to the control unit. A reference curve formed by the reference values will generally be displayed on the screen, usually together with the actual measuring curve. In the case of a hot seal a clear jump (discontinuity) will usually be visible in the measuring curve as a result of instantaneous softening of the foil parts to be attached to each other when a sufficiently high temperature is reached, whereby the clamping elements instantaneously move toward each other more quickly. It is usually advantageous to detect this discontinuity during the closing process, wherein the absence of the expected discontinuity generally indicates a defect in the seal. After the seal has been manufactured, possible irregularities in the seal, such as air bubbles, can optionally be detected using an infrared camera or other type of detection element, whereby the seal quality can be further determined Although it is possible to envisage positioning the at least one distance sensor at a distance from, and particularly above, the clamping elements, it is usually advantageous for the at least one distance sensor to be suitable for connection to a clamping element, whereby the distance measurement can take place with exceptional accuracy. Several types of distance sensor are suitable for use in the device according to the invention.

Since even small variations (defects) in the seal should preferably be detected, use is preferably made of a type of distance sensor with a relatively high accuracy (in the order of magnitude of micrometres). Non-limitative examples of applicable sensors are eddy current sensors, optical sensors and capacitive sensors. It is possible to envisage the at least one distance sensor comprising a plurality of mutually co-acting sensor parts. In a particular embodiment the at least one distance sensor comprises here at least one active sensor part and at least one passive sensor part. An active sensor part will here generally emit radiation, particularly electromagnetic radiation, and/or a field, particularly an electric and/or magnetic field, wherein the passive sensor part is adapted to reflect and/or disturb the generated radiation and/or the generated field. When the distance sensor is an optical sensor, the active sensor part comprises a light source and the passive sensor part comprises at least one reflector for reflecting a light beam emitted by the active sensor part.

In a preferred embodiment the device comprises at least two clamping elements for pressing against each other the foil and another part of the package to be attached to the foil. When the distance sensor comprises a plurality of sensor parts, it is advantageous for a clamping element to be provided with at least one first sensor part and the opposite clamping element to be provided with at least one second sensor part. Measuring the distance between the opposite outer ends of opposite clamping elements is recommended, irrespective of the type of distance sensor. It is particularly advantageous for the device to comprise a plurality of distance sensors for determining distances between different opposite parts of the clamping elements. The mutual distance between the clamping elements can in this way be determined in location-specific manner, this further enhancing the accuracy of the device. In a particular embodiment at least one clamping element is provided here at both outer ends with at least one distance sensor.

The other part of the package can be of diverse nature and can for instance be formed by a bottle or other type of container on which a foil has to be sealed. The device according to the invention will however usually be applied in and/or on a device for sealing foil packages (flow packs), wherein the other part of the package is formed by an (other) foil part. It is otherwise possible to envisage the device according to the invention forming an integral part of a device for sealing packages. It is therefore advantageous for the at least two clamping elements to be adapted to press two foil parts of the package against each other and mutually attach them, so forming a particularly airtight seal. The clamping elements will usually be formed here by clamping bars, also referred to as welding bars. The clamping bars extend substantially linearly here. It is usually advantageous for the mutually facing sides of the clamping elements to take an at least partially profiled form, this generally enhancing the quality of the seal to be formed.

Depending on the type of package, it can also be desirable to apply clamping elements taking a non-linear, particularly curved or angular, form.

The foil for sealing generally has a (single-layer) thickness of between 10 and 2000 micrometres, in particular between 20 and 2000 micrometres, depending on the nature and the material of the foil and depending on the type of seal to be realized. The seal can for instance be formed by material fusing under the influence of for instance heat (hot seal), ultrasonic radiation, an electric field, and/or using an adhesive (cold seal).

In a preferred embodiment the device comprises displacing means to enable relative displacement of the clamping elements, particularly between an opened position, in which the package to be sealed can be arranged between the clamping elements, and a closed position in which the clamping elements can seal the package. The displacing means for the relative displacement of at least one clamping element relative to the at least one other clamping element can be of very differing nature. It is possible here to envisage the displacing means functioning for instance pneumatically, hydraulically and/or electromechanically. In a typical situation the displacing means are adapted to exert a pressure of between 4 and 6 bar on the clamping elements, whereby a reliable and airtight seal can generally be manufactured. It is possible to envisage the control of the displacing means taking place by means of the above stated control unit. It is however also possible to envisage applying a separate control unit for controlling the displacing means, which separate control unit can for instance form an integral part of a packaging line. In the case the displacing means, and more preferably the clamping elements, form part of the device according to the invention, the device will also be suitable for sealing packages.

In a preferred embodiment the device comprises heat-generating means adapted to heat one or all clamping elements, whereby the foil will soften and will fuse with the other part of the package, particularly also formed by a foil, whereby an airtight seal can be formed. Such a type of seal is also referred to as hot seal.

The invention also relates to a method for detecting defects during sealing of a package comprising a foil, in particular by making use of a device according to the invention, comprising of: A) positioning between at least two clamping elements a foil and another part of the package to be connected to the foil, B) moving the clamping elements toward each other, wherein the connection between the foil and the other part of the package is formed, C) moving the clamping elements apart, and D) removing the package relative to the clamping elements, wherein the distance between the clamping elements is determined for a period during displacement of the clamping elements toward each other as according to step B), wherein the collected measured values are compared to predefined reference values. Advantages of the method have already been described at length in the foregoing.

In a preferred embodiment the method comprises step E), comprising of generating a signal when it is determined that at least one detected measured value exceeds at least one reference value. Generation of a signal can take place after the reference value has just been exceeded, but can also take place after the reference value has been exceeded by a determined absolute or relative (error) margin. It is also possible to envisage the signal only being generated when multiple measured values exceed the corresponding reference values, so that coincidental variations in a measured value do not immediately result in a signal being generated. The signal can for instance be of electrical, auditive and/or visual nature, and can for instance be formed by displaying a message on a screen. During step A) the other part of the package will usually be formed by a foil, whereby a foil seal is in fact manufactured. The seal can be welded here under the influence of increased temperature, but can also be glued. When heat is applied in order to realize the seal, at least one clamping element is heated during step B) to a typical temperature of between 90 and 200 degrees Celsius. A suitable pressure exerted on the clamping elements and to be transmitted to the foil and the other part of the package preferably lies between 4 and 6 bar. A typical duration of the closing process of the clamping elements, wherein the clamping elements are displaced from an opened position to a fully closed position, lies between 1 millisecond and 5 seconds.

It is advantageous here that the closing process, wherein the clamping elements are moved all the way toward each other from an opened position as according to step B), has a duration of x seconds, wherein the distance between the clamping elements is measured for between 0.2x and 5x seconds, particularly between 0.4x and 4x seconds. Alternatively, it is also possible to operate on the basis that the closing process, wherein the clamping elements are moved all the way toward each other from an opened position as according to step B), has a progression y, wherein the distance between the clamping elements is measured at least between 0.2y and y, particularly between 0.6y and y. Particularly the critical period of the closing process is in this way monitored. Particularly when a hot seal is manufactured, an instantaneous relative displacement of the clamping elements will occur as soon as the foil parts have become sufficiently soft to allow further displacement of the clamping elements, whereby the actual seal is manufactured. This instantaneous movement of the clamping elements is clearly visible as a discontinuity (bend) in the measuring curve formed by the measured values and will generally determine the quality of the hot seal. After the presence or absence of the expected instantaneous acceleration of the clamping elements has been detected, a message can also be generated so that the quality of the formed hot seal will be apparent at a glance.

An optional subsequent inspection, once the seal has been manufactured, can be formed by making an infrared image of the seal (step F), whereby possible irregularities (defects) are immediately made clearly visible. An infrared camera can be applied to make an infrared image. It is also possible to envisage applying other types of method to perform the subsequent inspection.

Figure 2:
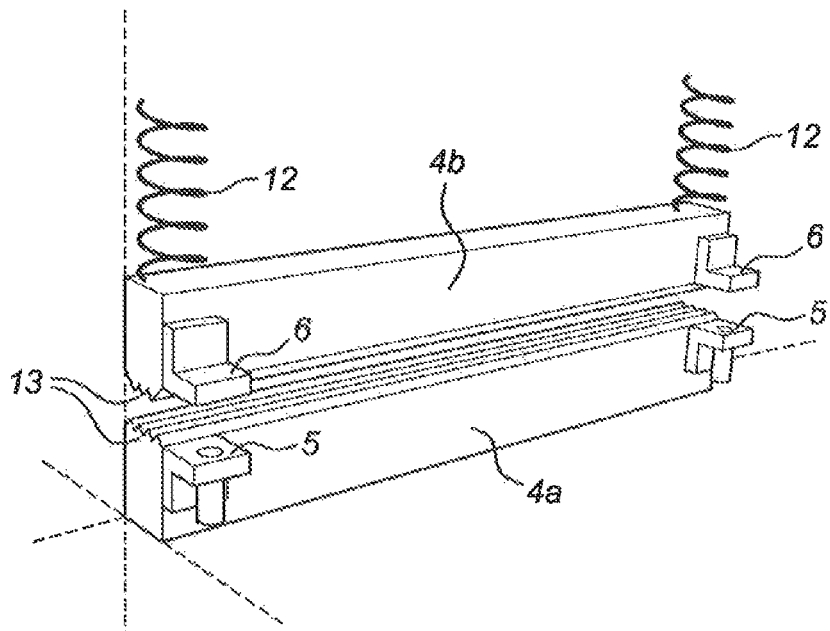
Figure 3:
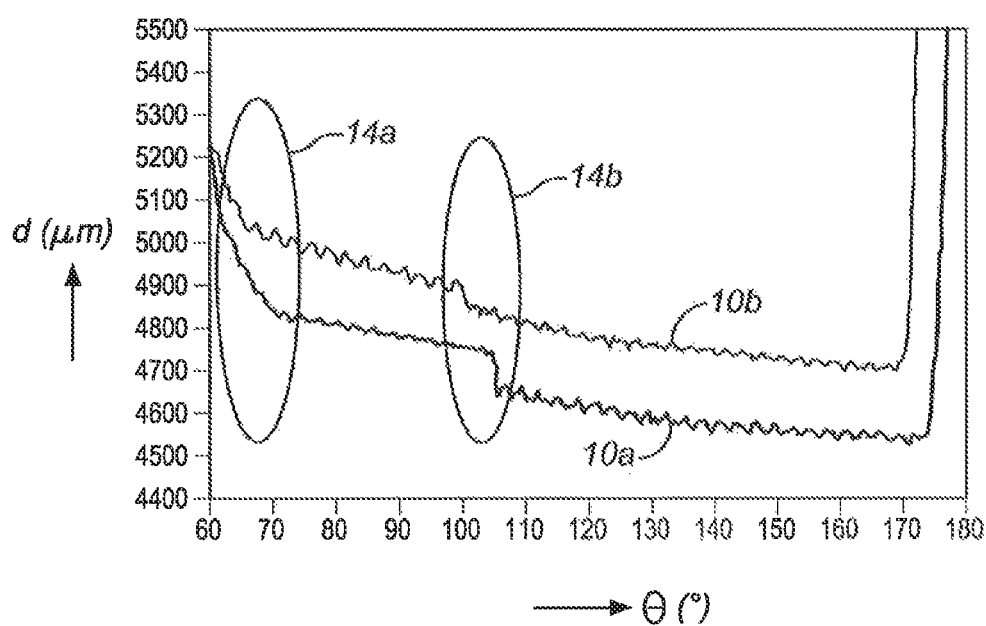

The invention will be elucidated on the basis of non-limitative exemplary embodiments shown in the following figures. Herein:

FIG. 1 is a schematic view of a device according to the invention adapted to perform the method according to the invention, FIG. 2 is a schematic view of an assembly of clamping bars and distance sensors connected to the clamping bars for use in the device according to FIG. 1, FIG. 3 shows an example of measuring curves generated during use of the device according to FIG. 1.

FIG. 1 is a schematic view of a device 1 according to the invention adapted to perform the method according to the invention. Device 1 is adapted to seal (close airtightly) a chips package 2. An open outer end 3 of a chips package 2 already provided with chips is positioned for this purpose between two relatively displaceable clamping bars 4a, 4b. Clamping bars 4a, 4b are provided at the outer ends with two distance sensors 5, 6, wherein each distance sensor comprises an active sensor part 5 and an opposite passive sensor part 6 to enable precise measurement of the distance d between clamping bars 4a, 4b. The active sensor part 5 can here comprise a light source and the passive sensor part 6 a reflector. Clamping bars 4a, 4b are adapted to be heated so that a (hot) seal 2a can be realized. Clamping bars 4a, 4b are connected for this purpose to heating means (not shown). Clamping bars 4a, 4b are shown in further detail in FIG. 2. At least one clamping bar 4b is coupled to an electric motor 7, this electric motor 7 being coupled to a control unit 8 in order to monitor the progress of the welding process. The active sensor part 5 of each distance sensor 5 is also coupled to the control unit in order to process the measured values collected by distance sensors 5, 6. The control unit is further coupled to a screen 9 for displaying the collected measured values in the form of a measuring curve 10. The quality of seal 2a can be determined by measuring the distance d between clamping elements 4a, 4b for a period during closing of clamping bars 4a, 4b, wherein the foil layers of chips package 2 are pressed onto each other. In the case the measured distance d differs significantly from predefined reference value(s) as a function of time and/or progression 2, this may indicate inclusion of air, liquid or solid matter in the seal, which will generally adversely affect the quality of seal 2a. If the predefined reference values are just exceeded, or with a minimal margin, a signal can be generated that the seal has one or more defects. After seal 2a has been manufactured, and chips package 2 thus closed, seal 2a can be inspected by means of infrared equipment 11 coupled to control unit 8. By making an infrared image of seal 2a it is possible to visualize with exceptional accuracy whether and, if so, where defects are present in seal 2a. Clamping bars 4a, 4b and electric motor 7 do not necessarily have to form part of device 1 according to the invention and can for instance form part of an already existing packaging line. It is also possible to envisage, and usually even advantageous, that distance sensors 5, 6 are coupled to their own control unit, this therefore being a control unit other than the control unit 8 adapted to control electric motor 7 and clamping bars 4a, 4b, whereby a modular detection device is in fact provided which can be arranged as modular unit on any similar packaging line.

FIG. 2 is a schematic view of an assembly of clamping bars 4a, 4b and active sensor parts 5 and passive sensor parts 6 connected to the clamping bars, wherein each couple of active sensor part and passive sensor part forms a distance sensor for use in device 1 according to FIG. 1. An eddy current sensor can be applied as possible active sensor part 5. FIG. 2 shows clearly that the mutually facing sides 13 of clamping bars 4a, 4b take a profiled form so as to enable improved grip on chips package 2 and, above all else, improved quality of seal 2a. One of the clamping bars 4b is coupled to two coil springs 12, which clamping bar 4a, 4b and/or which coil springs 12 are connected to electric motor 7 to enable displacement of said (mobile) clamping bar 4b relative to the opposite (stationary) clamping bar 4a to allow clamping of foil package 2.

FIG. 3 shows an example of measuring curves 10 generated during use of device 1 according to FIG. 1. FIG. 3 particularly shows two measuring curves 10a (lower measuring curve) and 10b (upper measuring curve), wherein the distance between clamping bars 4a, 4b is shown in micrometres (μm) as a function of the progression 2 expressed in degrees (°). It is assumed here that the overall closing process, i.e. the clamping bars 4a, 4b making a relative closing movement, begins at 0° and ends at 180°. In the shown example measured values are collected from only 60°, i.e. once ⅓ of the progression 2 has elapsed. It is of course possible to envisage monitoring beginning at other moments. The lower measuring curve 10a is representative of a closing process of clamping bars 4a, 4b wherein a chips package 2 is arranged between clamping bars 4a, 4b, wherein the formed seal 2a displays no defects. This measuring curve 10a can therefore be deemed representative of a normal closing process. The upper measuring curve 10b is representative of an (average) closing process of clamping bars 4a, 4b wherein a chips package 2 is arranged between clamping bars 4a, 4b but wherein contaminants such as chip particles are also present between foil parts of chips package 2 situated between clamping bars 4a, 4b, which contaminants may cause leakage in the seal and will impede normal closing of clamping bars 4a, 4b and will keep clamping bars 4a, 4b slightly further apart than is usual for the relevant stage of the closing process. This variation can be compared to the reference curve 10a and, if sufficiently exceeded, it is possible to determine that seal 2a displays defects which are too serious, whereby chips package 2 is removed from the production line of which the device forms part. Two ovals 14a, 14b have been drawn in the graph according to FIG. 3 in order to point to specific moments during the closing process. Shown in the left-hand oval 14a is the moment at which clamping bars 4a, 4b collide and thus close while clamping chips package 2. In the right-hand oval (at around 105) an instantaneous change in the distance between clamping bars 4a, 4b is visible in both measuring curves 10a, 10b, this being caused by the clamped foil parts of chips package 2 softening (becoming liquid), whereby fusing of the foil parts becomes possible and whereby displacement thereof toward each other is instantaneously made easier. This important moment is generally indicative of the quality of the final seal. If this typical pattern does not occur, or does so to lesser extent than shown in curve 10a, this generally indicates inclusions in seal 2a and thereby defects in seal 2a. It is thus also clearly apparent in this FIG. 3 that the upper curve 10b relates to a defective seal 2a, showing no sudden decrease in the distance between clamping bars 4a, 4b but another type of movement resulting from location-selective softening of chips package 2. Although comparing the measured values to predetermined reference values for a period during the closing process already enables relatively reliable detection of defects in seal 2a, it is particularly advantageous here to monitor how clamping bars 4a, 4b behave in relation to each other at the moment the foil parts have become sufficiently fluid.

It will be apparent that the invention is not limited to the exemplary embodiments shown and described here, but that within the scope of the appended claims numerous variants are possible which will be self-evident to the skilled person in the field.

What is claimed is:

1. A device for detecting defects during sealing of a package comprising a foil, comprising:
   at least one distance sensor for determining the distance between at least two relatively displaceable clamping elements for pressing against each other the foil and another part of the package to be attached to the foil, the distance sensor comprising active and passive sensor parts, the device configured to store a plurality of distance measurements between the at least two relatively displaceable clamping elements as collected measured distance values, and
   at least one control unit coupled to the at least one distance sensor for comparing the collected measured distance values collected by the distance sensor to a plurality of predefined reference measured values for a period as a function of time during displacement of the clamping elements toward each other,
   wherein the control unit is configured for monitoring an instantaneous change in the displacement of the clamping elements as a result of softening of the at least one foil.

2. The device as claimed in claim 1, further comprising a signal generator coupled to the control unit for generating a signal when the control unit determines that at least one detected measured value exceeds at least one reference value.

3. The device as claimed in claim 1, wherein the at least one control unit is configured for comparing the measured values collected by the distance sensor to predefined reference measured values for between 0.2x and 5x, wherein x ($R^+$) is a duration in seconds (s) of a closing process wherein the clamping elements are moved from an opened position all the way toward each other.

4. The device as claimed in claim 1, wherein the at least one control unit is configured for comparing the measured values collected by the distance sensor to predefined reference measured values for between 0.2y and y, wherein y ($R^+$) is a progression in degrees (°) of a closing process wherein the clamping elements are moved from an opened position all the way toward each other.

5. The device as claimed in claim 1, wherein the at least one distance sensor is formed by an optical sensor.

6. The device as claimed in claim 1, wherein the at least one distance sensor is formed by an eddy current sensor.

7. The device as claimed in claim 1, further comprising a plurality of distance sensors for determining distances between different opposite parts of the clamping elements.

8. The device as claimed in claim 1, further comprising heat-generating means adapted to heat at least one clamping element.

9. A method for detecting defects during sealing of a package comprising a foil, comprising:
   positioning a foil and another of part of a package to be connected to the foil between at least two clamping elements, wherein at least one of the at least two clamping elements is coupled to at least one coil spring,
   moving the clamping elements toward each other, wherein a connection between the foil and the other part of the package is formed, moving the clamping elements apart, and
removing the package relative to the clamping elements,
wherein the distance between the clamping elements is determined for a period as a function of time during displacement of the clamping elements moving toward each other, the distance between the different opposite parts of the clamping elements for the period being stored as a plurality of collected measured distance values,
wherein the collected measured values are compared to a plurality of predefined reference values, and
wherein an instantaneous change in the displacement of the clamping elements as a result of softening of the at least one foil is monitored.

10. The method as claimed in claim 9, further comprising generating a signal when it is determined that at least one detected measured value exceeds at least one reference value.

11. The method as claimed in claim 10, wherein the signal is generated when it is determined that multiple, detected, measured values exceed multiple, successive reference values.

12. The method as claimed in claim 9, wherein the foil and the other part of the package are welded to each other.

13. The method as claimed in claim 9, wherein at least one clamping element is heated to a temperature of between 90 and 200 degrees Celsius, wherein an instantaneous change in the displacement of the clamping elements as a result of softening of the at least one foil is monitored.

14. The method as claimed in claim 9, further comprising pressing the foil and the other part of the package onto each other for a duration of between 1 millisecond and 5 seconds.

15. The method as claimed in claim 9, further comprising a closing process, wherein the clamping elements are moved all the way toward each other from an opened position for a duration of x ($R^+$) seconds, wherein the distance between the clamping elements is measured for between 0.2x and 5x seconds.

16. The method as claimed in claim 9, further comprising a closing process, wherein the clamping elements are moved all the way toward each other from an opened position with a progression y ($R^+$) in degrees (°), wherein the distance between the clamping elements is measured at least between 0.2y and y degrees.

17. The method as claimed in claim 9, wherein the distance between the clamping elements is determined between different opposite parts of the clamping elements.

* * * * *